United States Patent [19]

Meyer

[11] Patent Number: 4,963,094
[45] Date of Patent: Oct. 16, 1990

[54] VACUUM CONTROLLER AND FILTER ASSEMBLY FOR DENTAL VACUUM SYSTEM

[75] Inventor: Robert A. Meyer, Spearfish, S. Dak.

[73] Assignee: Ramvac Corp., Spearfish, S. Dak.

[21] Appl. No.: 344,459

[22] Filed: Apr. 28, 1989

Related U.S. Application Data

[63] Continuation of Ser. No. 37,790, Apr. 13, 1987, abandoned.

[51] Int. Cl.⁵ ............................................. A61M 31/00
[52] U.S. Cl. ...................................... 433/95; 604/320; 604/319; 604/318; 604/317; 55/313; 55/420; 55/482
[58] Field of Search ...................... 433/92, 95; 55/313, 55/215, 315, 419, 420, 467, 482; 417/63, 36, 313, 202, 442, 503; 604/118, 119, 317, 316, 319, 320

[56] References Cited

U.S. PATENT DOCUMENTS

| | | | |
|---|---|---|---|
| 1,327,494 | 1/1920 | Sims | 55/420 X |
| 1,349,766 | 8/1920 | Hunt . | |
| 2,136,098 | 11/1938 | Browne . | |
| 2,170,074 | 8/1939 | Hewitt | 55/313 X |
| 2,264,616 | 12/1941 | Buckbee . | |
| 2,496,180 | 1/1950 | Smith et al. | 55/215 |
| 2,665,691 | 1/1954 | Ognanovich | 604/119 |
| 2,784,717 | 3/1957 | Thompson | 433/92 X |
| 2,812,895 | 11/1957 | Peeps . | |
| 2,895,220 | 7/1959 | Johnston et al. | 433/92 |
| 3,017,886 | 1/1962 | Thompson | 604/319 X |
| 3,078,579 | 2/1963 | Jones et al. . | |
| 3,138,873 | 6/1964 | Bishop | 433/92 |
| 3,191,600 | 6/1965 | Everett | 604/319 X |
| 3,308,609 | 3/1967 | McCulloch et al. . | |
| 3,429,313 | 2/1969 | Romanelli . | |
| 3,482,313 | 12/1969 | Stram . | |
| 3,780,502 | 12/1973 | Dupre et al. . | |
| 3,988,134 | 10/1976 | Gandrud . | |
| 4,013,076 | 3/1977 | Poderbaugh et al. | 604/320 |
| 4,133,658 | 1/1979 | Callewyn . | |
| 4,395,258 | 7/1983 | Wang et al. | 604/119 X |
| 4,580,978 | 4/1986 | Motola et al. | 433/95 X |
| 4,695,299 | 9/1987 | Spadaro et al. | 55/315 X |
| 4,726,825 | 2/1988 | Natale | 55/420 X |

FOREIGN PATENT DOCUMENTS

| | | | |
|---|---|---|---|
| 162138 | 10/1933 | Switzerland | 55/420 |
| 394252 | 6/1933 | United Kingdom | 433/92 |

OTHER PUBLICATIONS

WO 86/03669, Trawoger et al., 7/1986 (PCT/AT85/00057).

Primary Examiner—Carl D. Price
Attorney, Agent, or Firm—Nixon & Vanderhye

[57] ABSTRACT

A multi-function control component for use in dental vacuum systems includes, within a single housing, a vacuum control device for controlling the vacuum intensity within the system; a first air filter device for cleaning air permitted to enter the system by the vacuum control device; a second air filter for filtering gases flowing from an associated separating tank to a vacuum pump; a moisture detection device mounted in the housing for shutting down the vacuum pump drive motor upon detection of a predetermined level of moisture in the housing; a vacuum intensity measuring device; and a sealing device for sealing off the separating tank from the vacuum pump. The vacuum pump is a rotary vane pump, and is operatively connected to dental aspirator tips.

28 Claims, 1 Drawing Sheet

VACUUM CONTROLLER AND FILTER ASSEMBLY FOR DENTAL VACUUM SYSTEM

This is a continuation of application Ser. No. 07/037,790, filed Apr. 13, 1987, now abandoned.

BACKGROUND AND SUMMARY OF THE INVENTION

Modern dental care facilities usually include multiple operatories and a central vacuum system. Dental aspirator tips are provided at each operatory for disposition in the patient's mouth to remove aerosols, liquids, solid debris and odors. Typical conventional dental vacuum systems have been far from ideal from the standpoint of noise output, vacuum intensity, and flow rate characteristics, as well as efficiency and reliability. Typically, commercially available dental vacuum systems include a water ring or turbine type vacuum pump, usually with a backup pump specified due to the known unreliability of the primary pumps.

In applicant's co-pending application Ser. No. 477,519, filed Mar. 21, 1983, and hereby incorporated in this application by reference, a dental vacuum system is provided that overcomes most of the drawbacks associated with conventional, commercially marketed systems. The system disclosed in that application is characterized by low noise, excellent efficiency and ideal vacuum intensity and flow rate characteristics. The system also has excellent reliability and is easy to install and utilize in a central facility serving a number of dental operatories.

The system disclosed in my prior co-pending application includes a combined vacuum reservoir/separating tank operatively connected to a rotary vane vacuum pump which is in turn driven by a conventional motor. The rotary vane vacuum pump provides an effective vacuum intensity within a desirable range irrespective of the practical number of operatories connected thereto. In addition, the pump may be operated by a small motor, such as a one horsepower electrical motor, yet it can effectively serve the same number of operatories served by a much larger power source in conventional dental vacuum systems. The pump is preferably continuously lubricated utilizing an oil reservoir directly mounted thereon, and the pump and motor are mounted on a common platform in side-by-side relationship. A V-belt can interconnect pulleys of the pump and motor to provide forced transmission therebetween, and elastomeric feet are provided on the platform to facilitate noise control.

The vacuum reservoir/separating tank, which is operatively connected to dental aspirator tips at a plurality of dental operatories, preferably comprises a cylindrical tank with drain valve means, such as a rubber flap valve disposed at the bottom thereof. A support and drain assembly provides ready connection of the vacuum reservoir/separating tank to an external drain. The support and drain assembly includes a cylindrical support having a first end with an interior diameter slightly larger than the exterior diameter of the tank. Cooperating abutment portions on the tank and on the support and drain assembly operatively engage to limit the penetration of the tank into the support and drain assembly. A false bottom is provided in the support and drain assembly immediately below the rubber flap valve, and a drain pipe extends from an opening formed in the center low point of the false bottom through a side wall of the support and drain assembly. The drain pipe is readily connectable to the dental office's external sewer system. The second end of the support and drain assembly supports the vacuum tank on a horizontal surface in a generally upright position.

In my prior application, a conventional vacuum control unit is operatively attached to the reservoir/separation tank.

In accordance with the present invention, a unique multi-function control component replaces the conventional vacuum control unit, and is attached to the rotary vane vacuum pump between the pump and a separation tank generally similar to that described above.

Generally speaking, gases from the dental operatories (mainly air plus scavenged nitrous oxide and oxygen), separated from liquids and solids in the separation tank, flow through the control component of this invention to the rotary vane vacuum pump intake. Air is also permitted to enter the system through a vacuum controller in the control component and flows to the pump intake. The rotary vane vacuum pump, which is the propulsion source for the entire transport system, forces the arriving gases into an exhaust pipe for ultimate discharge to outside air.

The multi-function control component which is the subject of this invention, serves to: (1) control sealed vacuum (vacuum intensity with zero flow occurring) in the system to a preset maximum; (2) clean air that passes into the system through the sealed vacuum controller of the control component; (3) filter gas flow between the separating tank and the rotary vane vacuum pump; (4) detect moisture in the system downstream of the separation tank but upstream of the vacuum pump; (5) indicate the intensity of the system operating vacuum; and (6) seal the vacuum line between the separation tank and the control component when no vacuum is present.

With respect to the first mentioned control function, it is desirable to limit sealed suction of a dental vacuum system to avoid the inconvenience of aspirating tips sticking too tightly to lips, cheeks, tongue, rubber dams, etc. Some vacuum pumps, such as the positive displacement, rotary vane vacuum pump disclosed in my copending application and useable in conjunction with this invention, are capable of generating vacuum intensities in excess of 20 inches Hg. This is much higher than the 5 to 7 inches Hg considered appropriate for general dentistry applications. By limiting the sealed suction or vacuum, the control component of this invention allows a smaller motor to be used and protects the pump against overheating. Since motor horsepower requirements are dependent on flow rates and maximum vacuum, it will be appreciated that a pump having a design maximum vacuum intensity of 17 Hg, with no vacuum control, and under zero flow conditions, would exceed this design limit and require excessive motor horsepower. In accordance with this invention, the control component includes a vacuum controller containing a spring loaded valve that allows bypass air to enter the system through the control component if vacuum levels at the controller exceed a preselected maximum. Valve opening vacuum intensity may be set by adjusting a spring loaded nut in a manner which will be understood by those skilled in the art.

With respect to the cleaning function of the control component, environmental air may contain dust and debris which can adversely affect pump and vacuum controller life. A vacuum controller filter prevents these agents from entering the system by filtering bypass air before it reaches the vacuum controller. To accomplish this task, an easily removable, washable and/or replaceable foam filter element is placed over a perforated cylindrical metal backup screen placed around the upper part of the vacuum controller, which itself is located in an upper wall of the control component.

The control component also has a further filtering function made necessary because the flow from the separating tank, while comprised mainly of gases, may also contain small amounts of low density solids and some aerosols. In addition, under abnormal conditions such as tank overflow, the flow may contain liquids and/or large amounts of bubbles and/or foam. By preventing ingestion of liquids, solids, bubbles, and/or foam into the control component and vacuum pump, pump longevity is enhanced. Accordingly, the control component of this invention also includes a main air filter comprising an easily removable, washable and/or replaceable foam filter element which slips over a perforated cylindrical backup screen located in a main housing of the component. Access to the main air filter is made possible by dividing the housing of the control component into upper and lower portions with a suitable resilient sealing ring therebetween.

With respect to the detection function of the control component, it will be appreciated that during an abnormal condition of tank overflow, for example, the quantity of debris may rapidly overcome the capacity of the main air filter described above. It is therefore desirable to have a means of detecting excessive quantities of moisture (liquids, bubbles and/or foam) downstream of the separating tank but upstream of the rotary vane vacuum pump. Accordingly, an intrinsically safe moisture alarm system is also incorporated into the control component. This system is capable of detecting the presence of liquids, bubbles and/or foam in the control component housing assembly. It operates by lowering the electrical resistance between an alarm probe and its stainless steel holder. If, for example, the resistance is lowered to less than 47,000 ohms, after a two second time delay a signal is sent to a moisture alarm circuit board which then shuts down power to the vacuum pump drive motor and illuminates an alarm indicator light.

Regarding the control component indicator function, a vacuum gauge is attached within the main housing assembly for monitoring the system vacuum intensity, in order to assist in the adjustment of the vacuum controller.

Finally, in relation to the control component sealing function, it will be appreciated that when the rotary vane vacuum pump is turned off, stored vacuum existing in the separating tank and vacuum line plumbing will have tendency to rotate the pump in the opposite direction of its normal operation. This applies a vacuum to the pump exhaust side and could lead to the ingress of outside dust and/or debris into the pump from the exhaust line. Additionally, when the control component is opened for filter maintenance, foul odors from the separating tank could flow into the housing and escape into the environment. Therefore, a spring loaded check valve is built into the housing inlet so that when the vacuum pump is turned off, the vacuum intensity on the pump side of the valve decreases, causing the valve to close, thereby preventing the pump from "reverse motoring" and preventing tank odors from flowing into the control component and possibly out into the environment.

Further objects and advantages of the invention will become apparent upon inspection of the drawings and the detailed description of the invention which follows.

DETAILED DESCRIPTION OF THE INVENTION

Figure 1:
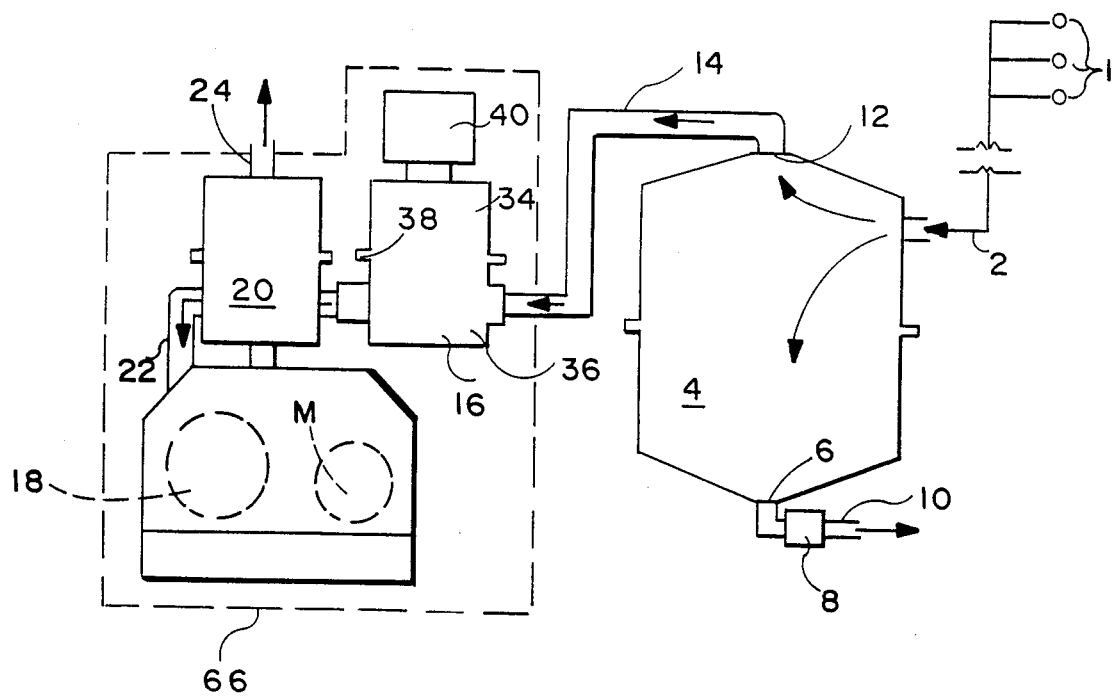
FIG. 1 is an overall schematic diagram of a dental vacuum system including a control component in accordance with this invention.

In FIG. 1, there is shown an overall schematic diagram of a dental vacuum system incorporating the control component of this invention. All materials moved by the vacuum system are picked up by the vacuum system's point of use, i.e., aspirators located in the oral cavity of a dental patient. Materials removed from this location include debris from tooth preparation, saliva, blood, water and large amounts of air. Other primary pickup locations may be, for example, nitrous oxide/oxygen nasal hoods, and vacuum drained sinks. When the vacuum lines are being flushed and cleaned, the primary pickup location may be a container of water or a vacuum cleaning solution.

Typically, materials from a plurality of aspirators 1 drain into a conduit 2 and flow into a separating tank 4. In the separating tank, liquids and solids drain into a outlet 6 located in the bottom of the tank, through a drain valve 8, and into a conduit 10 which leads to a sewer or other external disposal system. Gases within the separating tank 4 pass through an outlet 12 in the tank and are transported via conduit 14 into the control component 16 and thereafter to the vacuum pump 18 via conduit 22.

Vacuum pump 18 is provided with continuous lubrication means 20. This is a commercially available proprietary unit known as the L-3 Lubrication System manufactured by Babson Bros. Co. The gas flow to the pump from control component 16 is exhausted to outside air via conduit 24.

It will be understood that the vacuum pump may be driven, as in my prior, co-pending application, by a 1 h.p. electric motor M mounted adjacent the pump.

Figure 2:
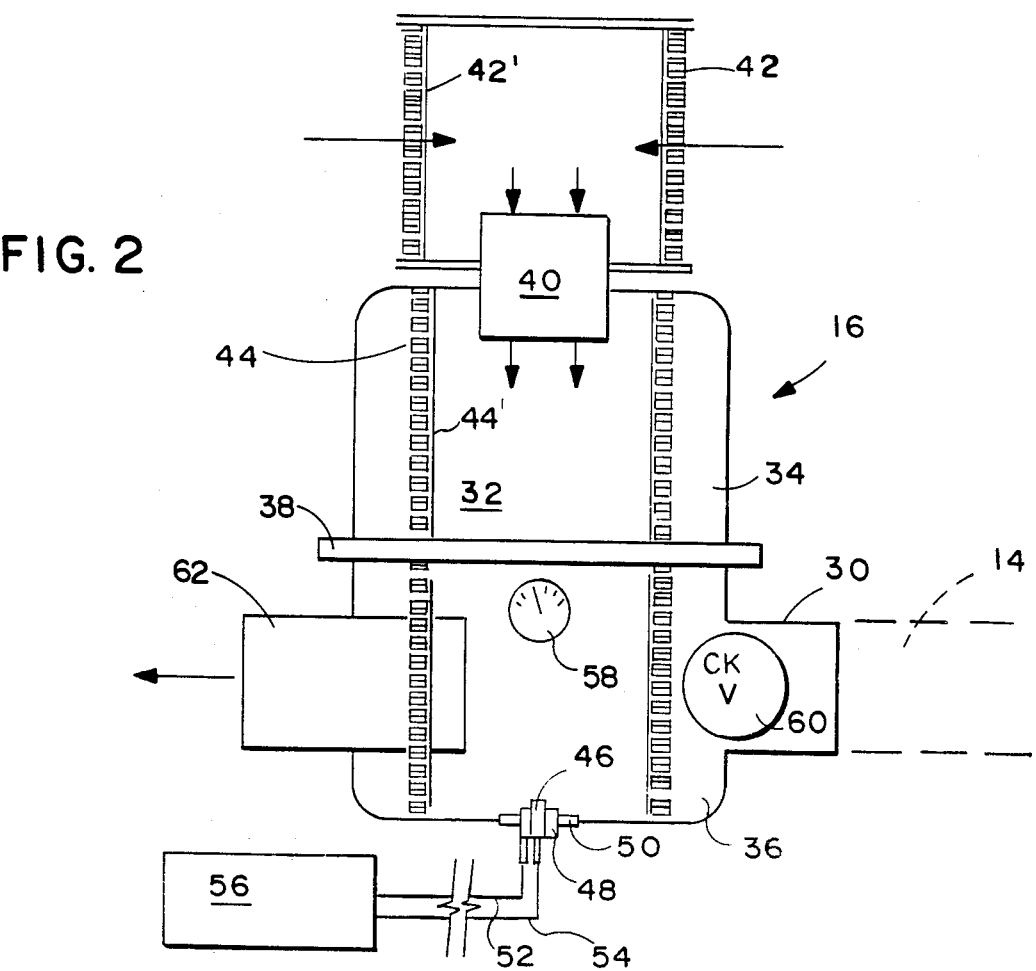
FIG. 2 is a detailed schematic diagram of a control component illustrated in FIG. 1.

Turning now to FIG. 2, the details of the control component 16 will be described in relation to each of its stated functions. As indicated previously, flow from the separator tank 4 is passed via conduit 14 to the control component. Flow enters the control component at an inlet 30 and enters a main housing 32 defined generally by an upper housing portion 34 and a lower housing portion 36 joined together along a seam which includes a rubber sealing ring 38.

The control component has a number of functions. Its primary function is to control the sealed vacuum intensity within the system. To this end, a vacuum controller assembly 40 is mounted above the housing. The vacuum controller 40 consists of a conventional spring loaded valve (details of which need not be shown) which, in this case, is utilized to permit entry of bypass air to enter the control component housing, when the vacuum level in the system exceeds a predetermined maximum. The vacuum intensity level required to open the valve may be adjusted in a conventional manner, for example, by turning a spring-loaded adjustment nut.

Because the vacuum controller may admit dirty air into the system, a vacuum control filter 42 is located about the upper portion of the vacuum controller 40. The filter 42 may be of any appropriate type, but is preferably an easily removable, washable and/or replaceable foam filter which is designed to slip over a perforated cylindrical metal backup screen 42". The size of the filter may be varied but preferably has an area of about 136 square inches.

The main housing formed by upper housing portion 34 and lower housing portion 36 encloses a main air filter 44 which, again, is preferably of the easily removable, washable and/or replaceable foam type which, as in the case of the vacuum controller filter, is designed to slip over a perforated cylindrical metal backup screen 44'. The main air filter serves to prevent ingestion of any solids or liquids, which might be present in the gas flow from the separating tank, into the vacuum pump.

The multi-function control component is also equipped to detect excessive quantities of moisture, for example, liquids, bubbles and/or foam downstream of the separating tank but upstream of the vacuum pump. This is especially useful to detect abnormal conditions, such as flooding of the separating tank 4. The moisture alarm detector includes alarm probe 46 enclosed within a stainless steel holder 48 and mounted within the bottom wall of the filter housing by means of a rubber grommet 50. Silicon rubber covered stainless steel conductors 52, 54, collectively connect the probe and holder to a moisture alarm relay circuit board 56. Upon detection of moisture in the control component in an amount sufficient to lower the electrical resistance between the probe and the stainless steel holder by a predetermined amount, e.g., to less than 47,000 ohms, then after a 2 second time delay, a signal is sent which causes the moisture alarm circuit board to shut down power to the vacuum pump drive motor M and to illuminate a moisture alarm indicator light (not shown).

The control component is further provided with a vacuum gauge 58, mounted within the housing 32, and preferably in the lower portion 34. The gauge quantifies system vacuum intensity and thereby assists in the adjustment of the vacuum controller valve.

A check valve 60 is included in the control component inlet 30 and enables the control component to perform its sealing function. The valve arrangement is such that when vacuum intensity in the control component is strong enough (as in normal pump operation) the check valve is open and permits flow to occur from the separating tank 4 to the control component 16. When the vacuum pump is turned off, the vacuum intensity on the pump side of the valve decreases, causing the valve to close. The incorporation of the check valve 60 in the inlet 30 is desirable because when the vacuum pump 18 is shut down, stored vacuum existing in the separating tank 4 and vacuum line plumbing has a tendency to rotate the pump in the opposite direction of its normal operation. This action applies vacuum to the exhaust side of the pump and could lead to the ingress of debris into the pump from the exhaust line 24. Moreover, when the control component is opened for maintenance, the closed check valve prevents free flow between the separating tank 4 and the filter housing 32 and thus prevents tank odors from escaping into the environment. Therefore, the check valve 60 is positioned in the control component inlet 30 to seal off the tank 4 from the control component upon shut down of the vacuum pump motor M.

The control component is further provided at its outlet end with an outlet 62 which passes gas flow to the vacuum pump 18.

In an exemplary embodiment of the invention, the control component 16 is located adjacent to the oiler 20. This enables the control component 16, vacuum pump 18, oiler 20 and motor M to be advantageously mounted together as a single power unit 66 located away from the separating tank 4.

It is thus seen that the present invention provides within a single housing, a control component which has no fewer than six functions, and which enhances the overall operation of any "dry" vacuum systems, that is, systems in which the vacuum pump does not intentionally contact any liquid.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A dental vacuum system comprising:
   a plurality of dental aspirator tips;
   a separation tank for receiving solid, liquid and gaseous materials from said aspirator tips and for separating the solids and the liquids from the gases;
   a vacuum pump for applying a vacuum to the system;
   a motor for driving said vacuum pump;
   vacuum conduit means interconnecting said plurality of dental aspirator tips and said separating tank;
   a vacuum line for carrying gases from said separation tank to said vacuum pump; and
   a multi-function control component housing located away from said separation tank and interposed directly in said vacuum line between said separation tank and said vacuum pump and through which gases from said separation tank flow via a gas inlet at one end of said housing and a gas outlet at the other end of said housing, said housing provided with first filter means intermediate said gas inlet and gas outlet for filtering flow from said separation tank, said housing having means for controlling suction within said system, and said housing further enclosing means for sealing said vacuum line upstream of said pump upon shut down of said motor.

2. A system as recited in claim 1 wherein said means for controlling suction within said system includes spring biased means for allowing bypass air to enter said control component housing when the vacuum exceeds a predetermined maximum.

3. A system as recited in claim 2 and wherein said control component housing further comprises second filter means disposed to filter said bypass air prior to entry into said control component housing.

4. A system as recited in claim 3 wherein said first filter means filters only flow entering said housing through said gas inlet, and said second filter means filters only bypass air entering said housing through said spring biased means.

5. A system as recited in claim 1 wherein said control component housing further encloses means for indicating system vacuum intensity.

6. A system as recited in claim 5 wherein said means for indicating system vacuum intensity comprises a vacuum gauge mounted in said control component housing.

7. A system as recited in claim 1 wherein said control component housing further encloses means for indicating moisture within said housing.

8. A system as defined in claim 7 wherein said moisture detecting means includes a moisture alarm probe located in a bottom wall of said housing.

9. A system as defined in claim 8 wherein said probe is secured within a stainless steel holder and mounted in said wall by means of a rubber grommet.

10. A system as defined in claim 9 wherein said alarm probe is effective, when actuated, to terminate power to said motor.

11. A system as recited in claim 1 wherein said vacuum pump is a rotary vane pump.

12. A system as recited in claim 1 wherein said sealing means comprises a check valve.

13. A system as recited in claim 1 wherein said control component housing is mounted adjacent said vacuum pump as part of a single power unit.

14. A dental vacuum system comprising:
a plurality of dental aspirator tips;
a separation tank for receiving solid, liquid and gaseous material from said aspirator tips and for separating the solids and the liquids from the gases;
a vacuum pump for applying a vacuum to the system;
a motor for driving said vacuum pump;
vacuum conduit means interconnecting said plurality of dental aspirator tips and said separation tank;
a vacuum line for carrying the gases from the separation tank to said vacuum pump; and
a multi-function control component housing located away from said separation tank and interposed directly in said vacuum line between said separation tank and said vacuum pump and through which gases from said separation tank flow via a gas inlet and a gas outlet in said housing, said housing provided with first filter means intermediate said gas inlet and gas outlet for filtering flow from said separation tank, said housing having means for controlling suction within said system, said housing further having means for terminating power to said motor upon detection of predetermined amounts of moisture within said control component housing, said power terminating means being located within said first filter means.

15. A dental vacuum system as recited in claim 14 wherein said terminating means includes a metal moisture alarm probe mounted in a wall of said control component housing.

16. A dental vacuum system as recited in claim 15 wherein said probe is mounted in a metal holder and wherein said terminating means is actuated when moisture in said housing causes the electrical resistivity between said probe and said holder to fall below a preselected value.

17. A system as recited in claim 14 wherein said means for controlling suction within said system includes spring biased means for allowing bypass air to enter said control component housing when the vacuum exceeds a predetermined maximum.

18. A system as recited in claim 14 and wherein said control component housing further comprises second filter means disposed to filter said bypass air prior to entry into said control component.

19. A system as recited in claim 14 wherein said vacuum pump is a rotary vane pump.

20. A system as recited in claim 14 wherein said control component housing further encloses means for indicating system vacuum intensity.

21. A multi-function control component for use in dental vacuum system which includes a plurality of dental operatories connected to a separating tank, a vacuum pump and a motor for driving said pump, said control component comprising:
(a) a housing located remote from said separating tank and provided with an inlet end adapted to be connected to a vacuum line from the separating tank, and an outlet end adapted to be connected to a vacuum line to the vacuum pump such that gas flow from the separating tank flows through said housing;
(b) first valve means in said inlet end of said housing responsive to vacuum intensity;
(c) second valve means mounted in a wall of said housing adapted to open to permit entry of bypass air in response to a vacuum level exceeding a predetermined maximum;
(d) means in said housing for indicating moisture in said housing; and
(e) first filter means adapted to filter flow between said inlet end and said outlet end.

22. A multi-function control component as defined in claim 20 and wherein said housing encloses first filter means adapted to filter flow between said inlet end and said outlet end.

23. A multi-function control component as defined in claim 21 and further including means for indicating intensity of vacuum in said housing.

24. A multi-function control component as recited in claim 21 wherein said second valve means is adapted to control the sealed vacuum in the system and comprises an adjustable, a spring loaded check valve.

25. A multi-function control component as defined in claim 24 wherein said component further comprises second filter means located upstream of said spring loaded check valve.

26. A multi-function control component as defined in claim 21 wherein said first valve means comprises a check valve mounted in said inlet end of said housing.

27. A multi-function control component as defined in claim 21 wherein said moisture indicating means comprise a moisture alarm probe located in said housing, operatively connectable to circuit means for terminating power to the motor upon detection of predetermined amounts of moisture in said housing.

28. A system as recited in claim 3 wherein said housing comprises upper and lower portions joined together about a sealing ring, said first filter means being enclosed by said housing, and said second filter means located above said upper portion of said housing.

* * * * *